US012171728B2

(12) United States Patent
Fioretti et al.

(10) Patent No.: US 12,171,728 B2
(45) Date of Patent: Dec. 24, 2024

(54) MIXTURE OF RESVERATROL SUPPORTED ON METAL HYDROXIDE AND NON-SUPPORTED PURE RESVERATROL FOR TREATING FEMALE FERTILITY

(71) Applicant: S&R FARMACEUTICI S.P.A., Bastia Umbra (IT)

(72) Inventors: Bernard Fioretti, Foligno (IT); Lucio Leonardi, Gualdo Cattaneo (IT)

(73) Assignee: S&R FARMACEUTICI S.P.A., Bastia Umbra (IT)

( * ) Notice: Subject to any disclaimer, the term of this patent is extended or adjusted under 35 U.S.C. 154(b) by 221 days.

(21) Appl. No.: 17/048,029

(22) PCT Filed: Apr. 16, 2019

(86) PCT No.: PCT/IB2019/053137
§ 371 (c)(1),
(2) Date: Oct. 15, 2020

(87) PCT Pub. No.: WO2019/202508
PCT Pub. Date: Oct. 24, 2019

(65) Prior Publication Data
US 2021/0169825 A1 Jun. 10, 2021

(30) Foreign Application Priority Data

Apr. 16, 2018 (IT) .................. 102018000004540

(51) Int. Cl.
| | | |
|---|---|---|
| A61K 31/05 | (2006.01) |
| A23L 29/00 | (2016.01) |
| A23L 33/10 | (2016.01) |
| A61K 33/08 | (2006.01) |
| A61K 45/06 | (2006.01) |
| A61K 31/4415 | (2006.01) |
| A61K 31/593 | (2006.01) |
| A61K 31/714 | (2006.01) |

(52) U.S. Cl.
CPC ............ *A61K 31/05* (2013.01); *A23L 29/035* (2016.08); *A23L 33/10* (2016.08); *A61K 33/08* (2013.01); *A61K 45/06* (2013.01); *A61K 31/4415* (2013.01); *A61K 31/593* (2013.01); *A61K 31/714* (2013.01)

(58) Field of Classification Search
CPC .............................. A61K 31/05; A61K 33/08
See application file for complete search history.

(56) References Cited

U.S. PATENT DOCUMENTS

| | | | |
|---|---|---|---|
| 5,462,946 | A | 10/1995 | Mitchell et al. |
| 5,663,202 | A | 9/1997 | Horrobin et al. |
| 8,383,165 | B1 | 2/2013 | Andrews |
| 11,246,834 | B2 | 2/2022 | Fioretti et al. |
| 2010/0286247 | A1 | 11/2010 | Gilchrest et al. |
| 2011/0269776 | A1 | 11/2011 | Miller |
| 2013/0260217 | A1 | 10/2013 | Matsui et al. |
| 2017/0312251 | A1 | 11/2017 | Munson |
| 2019/0125675 | A1 | 5/2019 | Fioretti et al. |
| 2022/0023274 | A1 | 1/2022 | Fioretti et al. |
| 2022/0395460 | A1 | 12/2022 | Fioretti et al. |

FOREIGN PATENT DOCUMENTS

| | | |
|---|---|---|
| CN | 1539419 A | 10/2004 |
| EP | 2679243 A1 | 1/2014 |
| EP | 2875809 A1 | 5/2015 |
| EP | 3130336 A1 | 2/2017 |
| FR | 3125409 A1 | 1/2023 |
| IN | 1312MU2014 | 10/2015 |
| JP | 2013211228 A | 10/2013 |
| WO | 2006/013602 A1 | 2/2006 |
| WO | 2009/029887 A1 | 3/2009 |
| WO | 2012/107905 A1 | 8/2012 |
| WO | 2013/076121 A1 | 5/2013 |
| WO | 2013/152055 A1 | 10/2013 |
| WO | 2017/179012 A1 | 10/2017 |
| WO | 2018/065900 A1 | 4/2018 |
| WO | 2019/202508 A1 | 10/2019 |
| WO | 2020/128802 A1 | 6/2020 |
| WO | 2021/261062 A1 | 12/2021 |
| WO | 2023/007088 A1 | 2/2023 |

OTHER PUBLICATIONS

Arner J. R. et al., "myo-Inositol oxygenase: molecular cloning and expression of a unique enzyme that oxidizes myo-inositol and D-chiro-inositol" *Biochem J.*, 2001, pp. 313-320.

Consolidated List of Citations by Opposition for European Application No. 17727376.0 filed on Apr. 13, 2017 on behalf of S& Farmaceutici S.P.A.

Costantino D. et al., "Metabolic and hormonal effects of myo-inositol in women with polycystic ovary syndrome: a double-blind trial" *European Review for Medical and Pharmacological Sciences*, 2009, pp. 105-110.

Feng R. et al., "Transforming berberine into its intestine-absorbable form by the gut microbiota." *Ski Rep.* Jul. 2015, 15; 5:12155.

Hyderali B. N. et al., "Oxidative stress and cardiovascular complications in polycystic ovarian syndrome" *Eur J Obstet Gynecol Reprod Biol.* Aug. 2015;191:15-22. doi: 10.1016/j.ejogrb.2015.05.005. Epub Jun. 2, 2015. PMID: 26066290.

Indian Application No. 1766/CHE/2007 filed on Aug. 9, 2007 on behalf of J. Srinivasan and K. Gopalakrishnan. Published as IN2007CH01766A on Feb. 24, 2012. 16 pages.

(Continued)

*Primary Examiner* — Kevin E Weddington
(74) *Attorney, Agent, or Firm* — Steinfl + Bruno LLP

(57) ABSTRACT

A formulation of a dietary supplement for the improvement of female fertility in the human species based on the use of a definite stoichiometry of resveratrol with different pharmacokinetic profiles is described. The mixture is used alone or in combination with nutrients with antioxidant properties and not, used in female subfertility such as N-acetil-cysteine; Melatonin Vitamins A, C, D, E, B2, B3, B6, B12, folic acid, inositol, zinc, selenium, Coenzyme QIO, A-lipoic acid, arginine and *Lycium barbarum* berry extracts.

18 Claims, 1 Drawing Sheet

(56) References Cited

OTHER PUBLICATIONS

International Preliminary Report on Patentability for International Application No. PCT/IB2019/053137 filed on Apr. 16, 2019 on behalf of S&R Farmaceutici S.P.A. Mail Date: Oct. 20, 2020, 7 pages.
International Preliminary Report on Patentability for International Application No. PCT/IB2019/060873 filed on Dec. 16, 2019 on behalf of S&R Farmaceutici S.P.A. Mail Date: Jun. 16, 2021, 7 pages.
International Search Report for International Application No. PCT/IB2019/060873 filed on Dec. 16, 2019 on behalf of S&R Farmaceutici S.P.A. Mail Date: Aug. 12, 2020 3 pages.
Italian Application 102016000038243 filed on Apr. 13, 2016 on behalf of S&R Farmaceutici S.P.A. 33 pages.
Italian Application No. 0001391323 filed on Apr. 20, 2007 on behalf of Lloyds International Credit LLC 74 pages.
Kabiri N. et al., "Lipid lowering by hydro extracts of *Amaranthus caudatus* L. induces regression of rabbits atherosclerotic lesions." *Lipids Health Dis.* May 2011, 5 28; 10:89.
Knott E.J. et al., "Fenugreek supplementation during high-fat feeding improves specific markers of metabolic health." *Ski Rep.* Oct. 2017, 6;7(1): 12770.
Kong W. et al., "Berberine is a novel cholesterol-lowering drug working through a unique mechanism distinct from statins." *Nat Med.* Dec. 2004; 10(12):1344-51.
Lee K. et al., "Effects of potato and lotus leaf extract intake on body composition and blood lipid concentration." *J Exerc Nutrition Biochem.* Mar. 2015;19(1): 25-30.
Macut D. et al., "Dyslipidemia and oxidative stress in PCOS" *Front Horm Res.* 2013;40:51-63. doi: 10.1159/000341683. Epub Oct. 1, 20128. PMID: 24002405.
Cambridge Dictionary. (2023). miscela—translate into English with the Italian-English Dictionary—Cambridge Dictionary. https://dictionary.cambridge.org/us/dictionary/italian-english/miscela, 6 pages.
Minozzi M. et al., "The combined therapy myo-inositol plus D-Chiro-inositol, in a physiological ratio, reduces the cardiovascular risk by improving the lipid profile in PCOS patients" *European Review for Medical and Pharmacological Sciences*, 2013, pp. 537-540.
Notice of Allowance for U.S. Appl. No. 16/093,295, filed Oct. 12, 2018, on behalf of S&R Farmaceutici S.P.A. Mail Date: Sep. 30, 2021. 10 Pages.
Parazinni F. "Resveratrol, inositol, vitamin D and K in the prevention of cardiovascular and osteoporotic risk: a novel approach in peri- and postmenopause" *Minerva Ginecologica*, vol. 66 No. 5, Oct. 2014, pp. 513-518.
Ried K. et al., "Effect of garlic on serum lipids: an updated metanalysis." Nutr Rev. May 2013;71(5): 282-99.
Rop O. et al., "Beta-glucans in higher fungi and their health effects." Nutr Rev. Nov. 2009;67(11): 624-31.
Saleem Q. et al., "Lipogels: Single-Lipid-Bilayer-Enclosed Hydrogel Spheres" *Biomacromolecules*, 12, 6, May 2011, 7 pages.
S&R Farmaceutici Newsletter—https://www.srfarmaceuticl.it/nl10-28-june-2016/?lang=en Article Date: Jun. 28, 2016, 5 pages.
S&R Farmaceutici Newsletter—https://www.srfarmaceuticl.it/nl14-16-settembre-2016/ Article Date: Sep. 16, 2016, 3 pages.
Spogli R. et al., "Solid Dispersion of Resveratrol Supported on Magnesium DiHydroxide (Resv@MDH) Microparticles Improves Oral Bioavailability" Nutrients, 10(12):1925. Dec. 2018, 10 pages.
Unfer V. et al., "Updates on the myo-inositol plus D-chiro-inositol combined therapy in polycystic ovary syndrome" *Expert Rev. Clin. Pharmacol*, 2014, pp. 623-631.
Written Opinion for International Application No. PCT/IB2019/060873 filed on Dec. 16, 2019 on behalf of S&R Farmaceutici S.P.A. Mail Date: Aug. 12, 2020 6 pages.
Agarwal, A., et al. "Oxidative stress and its implications in female infertility—a clinician's perspective" *Reproductive BioMedicine Online*11(5), 641-650, (Aug. 2005).
Asplin, I., et al. "chiro-Inositol deficiency and insulin resistance: A comparison of thechiro-inositol- and theimyo-inositol-containing insulin mediators isolated from urine, hemodialysate, and muscle of control and type II subjects"*PNAS*90, 5924-5928, (Jul. 1993).
Baillargeon, J-P., et al. "Altered D-Chiro-Inositol Urinary Clearance in Women with Polycystic Ovary Syndrome" Diabetes Care 29(2), 300-302, (Feb. 2006).
Bates, S. H., et al. "Insulin-like effect of pinitol" British Journal of Pharmacology 130, 1944-1948, (2000).
Benrick, A., et al. "Resveratrol Is Not as Effective as Physical Exercise for Improving Reproductive and Metabolic Functions in Rats with Dihydrotestosterone-Induced Polycystic Ovary Syndrome" *Evidence-Based Complementary Alternative Medicine*2013: 964070, (2013). 13 pages.
Chiu, T., et al. "Follicular fluid and serum concentrations of myo--inositol in patients undergoing IVF: relationship with oocyte quality" *Human Reproduction*17(6), 1591-1596, (2002).
De Leo, V., et al. "Evaluation of the treatment with D-Chiroinositol on levels of oxidative stress in PCOS patients" *Minerva Ginecologica*64(6), 531-538, (2012). (English + Original).
Ehrmann, D. A. "Polycystic ovary syndrome" *New England Journal of Medicine*352, 1223-1236, (2005).
Female infertility but not only . . . discover the polycystic ovary syndrome, *S&R Farmaceutici*, Jun. 2016.
Fioretti, B., et al. "Revifast: Resveratrol Spring Form for Increasing Bioavailability". *L'integratore nutrizionale* 2013, 16(3): 9-14. (English + Original).
Grundy, S. M., et al. "Diagnosis and Management of the Metabolic Syndrome: An American Heart Association/National Heart, Lung, and Blood Institute Scientific Statement" *American Heart Association; National Heart, Lung, and Blood Institute.* Circulation. 112(17), 2735-2752, (2005).
Hopkinson, Z. E., et al. "Polycystic ovarian syndrome: the metabolic syndrome comes to gynaecology" *BMJ*317, 329-332 (Aug. 1998).
International Search Report for International Application No. PCT/IB2017/052151 filed Apr. 13, 2017 on behalf of S&R Farmaceutici S.P.A. Mail date: Jul. 13, 2017. 4 pages.
International Search Report for International Application No. PCT/IB2019/053137 filed on Apr. 16, 2019 on behalf of S&R Farmaceutici S.P.A. Mail Date: Aug. 13, 2019 4 pages.
Jung, T-S., et al. "Determination of Urinary Myo-/Chiro-Inositol Ratios from Korean Diabetes Patients"*Yonsei Medical Journal*46(4), 532-538, (2005).
Kennington, A.S., et al. "Low Urinary chiro-Inositol Excretion in Non--Insulin-Dependent Diabetes Mellitus" New England Journal of Medicine 323(6), 373-378, (Apr. 1990).
Larner, J. "D-Chiro-Inositol—Its Functional Role in Insulin Action and Its Deficit in Insulin Resistance" *International Journal of Experimental Diabetes Research*3, 47-60, (2002).
Larner, J., et al. "D-Chiro-Inositol Glycans in Insulin Signaling and Insulin Resistance" *Molecular Medicine*16(11-12), 543-551, (Nov. 2010). 10 pages.
Larner, J., et al. "Urinary myo-Inositol-to-chiro-Inositol Ratios and Insulin Resistance"*Diabetes Care*19(1), 76-78, (Jan. 1996).
Ostlund, Jr., R. E., et al. "D-chiro-Inositol metabolism in diabetes mellitus"*PNAS*90, 9988-9992, (Nov. 1993).
Papalou, O., et al. "Oxidative Stress in Polycystic Ovary Syndrome" *Current Pharmaceutical Design*22(18), 2709-2722, (2016).
Pinar, H. K., et al. "Statins: Do they have potential in the treatment of polycystic ovary syndrome?" *Seminars in Reproductive Medicine*26(1), 127-138, (Jan. 2008). 25 pages.
Ragonese F et al., "Resveratrol-Mg hydroxide complex display enhanced bioavailability: A possible application in DM-1 disease." Journal of Biotechnology, vol. 256, 2017.
Ruiz-Sanz, J. I., et al. "Ala16Val SOD2polymorphism is associated with higher pregnancy rates in in vitro fertilization cycles"*Fertility and Sterility*95(5), 1601-1605, (Apr. 2011).
Stull, A. J., et al. "Effects of Acute Pinitol Supplementation on Plasma Pinitol Concentration, Whole Body Glucose Tolerance, and Activation of the Skeletal Muscle Insulin Receptor in Older Humans" *Hormone and Metabolic Research*41(5), 381-386, (May 2009). 14 pages.

(56) References Cited

OTHER PUBLICATIONS

The Rotterdam ESHRE/ASRM-Sponsored PCOS Consensus Workshop Group. "Revised 2003 consensus on diagnostic criteria and long-term health risks related to polycystic ovary syndrome" *Fertility and Sterility* 81(1), 19-25, (Jan. 2004).
Written Opinion for International Application No. PCT/IB2017/052151 filed Apr. 13, 2017 on behalf of S&R Farmaceutici S.P.A. Mail date: Jul. 13, 2017. 8 pages.
Written Opinion for International Application No. PCT/IB2019/053137 filed on Apr. 16, 2019 on behalf of S&R Farmaceutici S.P.A. Mail Date: Aug. 13, 2019 6 pages.
Anonymous: "Eulipid", Jan. 1, 2019 (Jan. 1, 2019), XP055607781, Retrieved from the Internet: URL: https://www.uganutraceuticals.com/product/eulipid, 1 page.
Anonymous: "Eulipid", Nov. 26, 2018 (Nov. 26, 2018), XP055607652, Retrieved from the Internet: URL: https://web.archive.org/web/20181126013144/https://www.uganutraceuticals.com/, 1 page.
Anonymous: "Faros", Sep. 25, 2017 (Sep. 25, 2017), XP055607715, Retrieved from the Internet: URL: https://web.archive.org/web/20170925061342/http://pro.fidiapharma.com/it/tutti-i-prodotti/integratori-alimentari/faros,21,246, 1 page.
Anonymous: "Il colesterolo alto e nemico della salute del cuore. Ecco come combatterlo", Jun. 15, 2018 (Jun. 15, 2018), XP055607783, Retrieved from the Internet: URL: https://www.omegor.com/blogomega-3/omega-3-cuore/colesterolo-alto-nemico-della-salute-del-cuore/, 1 page.
Attia E.S. et al., "The hypoglycemic and antioxidant activities of garden cress (*Lepidium sativum* L.) seed on alloxan-induced diabetic bad rats." *Nat Prod Res*. Dec. 2017, 13:1-5.
Liu C.S. et al., "Research progress on berberine with a special focus on its oral bioavailability." *Phytotherapy*. Mar. 2016; 109:274-282.
Panico A. et al., "Endocrine effects of two different treatments in polycystic ovary syndrome" Giornale Italiano Di Ostetricia E Ginecologia, vol. 38, No. 4, Jul. 1, 2016, p. 364-370, English Abstract.
Sahebkar A. "Effects of resveratrol supplementation on plasma lipids: a systematic review and meta-analysis of randomized controlled trials." *Nutr Rev*. Dec. 2013; 71(12): pp. 822-835.
Sandro Magnanelli: "Eu lipid 30cpr: Scheda Tecnica del Parafarmaco", Sep. 1, 2018 (Sep. 1, 2018), XP55607659, Retrieved from the Internet: URL:https://www.torrinomedica.it/parafarmaci/monografie/eulipid_30cpr/, 1 page.
Badawy A et al., "N-Acetyl cysteine and clomiphene citrate for induction of ovulation in polycystic ovary syndrome: a cross-over trial." Acta Obstet Gynecol Scand. 2007; 86(2):218-22.
Communication under Rule 71(3) EPC for EP Application No. 17727376.0 filed on Apr. 13, 2017 on behalf of S& Farmaceutici S.P.A. Mail Date: Jan. 13, 2021 18 pages.
Dattilo M. et al., "Improvement of gamete quality by stimulating and feeding the endogenous antioxidant system: mechanisms, clinical results, insights on gene-environment interactions and the role of diet." J Assist Reprod Genet. Dec. 2016;33(12):1633-1648.
Evers J.L. "Female subfertility." Lancet. Jul. 13, 2002;360(9327):151-9).
Gaskins A.J. et al., "Earth Study Team. Association between serum flurries and vitamin B-12 and outcomes of assisted reproductive technologies." Am J Clin Nutr. Oct. 2015; 102( 4):943-50.
Grajecki D. et al., "The effect of micronutrient supplements on female fertility: a systematic review." Arch Gynecol Obstet. May 2012; 285(5): 1463-71. doi: 10.1007/s00404-012-2237-2.
Ledee-Bataille N. et al., "Combined treatment by pentoxifylline and tocopherol for recipient women with a thin endometrium enrolled in an oocyte donation programme." Hum Reprod. May 2002; 17(5): 1249-53.
Lerchbaum E. et al., "Vitamin D and Fertility: a systematic review." Eur J Endocrinol. May 2012; 166(5):765-78.
Liu M. et al., "Resveratrol protects against age-associated infertility in mice." Hum Reprod. Mar. 2013; 28(3):707-17.
Nestler J.E et al., "Insulin stimulates testosterone biosynthesis by human thecal cells from women with polycystic ovary syndrome by activating its own receptor and using inositolglycan mediators as the signal transduction system." J Clin Endocrinol Metab. Jun. 1998; 83(6):2001-5.
Non-Final Office Action for U.S. Appl. No. 16/093,295, filed Oct. 12, 2018 on behalf of S&R Farmaceutici S.P.A. Mail Date: Nov. 13, 2020. 13 Pages.
OZCAN P. et al., "Can Coenzyme Q10 supplementation protect the ovarian reserve against oxidative damage?" J Assist Reprod Genet. Sep. 10, 2016;33(9): 1223-30.
Panico A. et al., "Endocrine effects oftwo different treatments in polycystic ovary syndrome" Giornale Italiano Di Ostetricia E Ginecologia, vol. 38, No. 4, Jul. 1, 2016, p. 357-358.
Showell M.G. et al., "Antioxidants for female subfertility." *Cochrane Database Syst Rev*. Jul. 28, 2017;7:CD007807.
Tatone C. et al., "Sirtuins in gamete biology and reproductive physiology: emerging roles and therapeutic potential in female and male infertility." Hum Reprod Update. 2018. pp. 1-23.
Anonymous: "Madhu" Aug. 2022 (Aug. 3, 2022) Difference Between, Retrieved from the Internet: URL: https://www.differencebetween.com/what-is-the-difference-between-resveratrol-and-grape-seed-extract/.
Ma, Z. et al., "Phytochemical Constituents, Health Benefits, and Industrial Applications of Grape Seeds: A Mini-Review," antioxidants, Sep. 15, 2017, 6, 71, 11 pages.
Amaral A et al, "Mitochondria functionality and sperm quality." Reproduction. Oct. 1, 2013;146(5):R163-74. 12 pages.
Amended claims before examination for EP Application No. 19836541.3, Mail Date: Nov. 25, 2023, 5 Pages.
Anonymous, "Dalla Ricerca S&R Farmaceutici nell'ambito della Scienza della Riproduzione," S&R Farmaceutici, 2020. 6 pages.
Anonymous, Genante di vita leaflet, S&R Farmaceutici, 2023. 2 pages.
Anonymous, "Genante di Vita," S&R Farmaceutici, 2023, 8 pages.
Anonymous, "Genante, Evidenze Scientifiche," S&R Farmaceutici, 2023. 1 page.
Anonymous, "Genante, nella Fertilita Maschile," S&R Farmaceutici, 2023. 1 page.
Anonymous, "Genante Nutraceutical Dossier," S&R Farmaceutici, Feb. 2023, 142 pages.
Anonymous, "Genante, Unta forte correlazione tra motilita spermatica e potenziale elettrico Mitocondriale," S&R Farmaceutici, 2023. 1 page.
Anonymous, "Il nutaceutico brevettato con il piu alto numero di evidenze scientifiche per la fertilita di coppia," 2023, 8 pages.
Anonymous, "Il Resveratrolo aumenta l'attività metabolica mitocondriale delle cellule della granulosa," S&R Farmaceutici, 2020. 4 pages.
Anonymous, "Sinopsi Genante," S&R Farmaceutici, 2023, 1 page.
Anonymous, "Linea Guida intervista, Genante," S&R Farmaceutici, 2023. 1 page.
Anonymous, "Revifastdol", Retrieved from the internet: https://www.srfarmaceutici.it/revifastdol/?lang=en [retrieved on Feb. 29, 2024].
Article 67(3) Communication for EP Application No. 19836541.3, Mail Date: Apr. 7, 2022, 6 Pages.
Bahramrezaie et al. "Effects of resveratrol on VEGF & HIF1 genes expression in granulosa cells in the angiogenesis pathway and laboratory parameters of polycystic ovarysyndrome: a triple-blind randomized clinical trial." J Assist Reprod Genet 2019; 36:1701-12. 910. 12 pages.
Battaglia, et al. "Resveratrol Treatment Induces Mito-miRNome Modification in Follicular Fluid from Aged Women with a Poor Prognosis for In Vitro Fertilization Cycles," Antioxidants, May 2022, 11, 1019. 13 pages.
Cheng Y. et al., "Astragalus polysaccharides lowers plasma cholesterol through Mechanisms Distinct from Statins" PLoS One, vol. 6 No. 11, Nov. 2011, pp. 1-9.
Communication of a Notice of Opposition to EP Application No. 17727376.0, Mail Date: Mar. 31, 2022, 27 Pages.
Communication of Opposition Proceedings for EP Application No. 17727376.0, Mail Date: Aug. 26, 2022, 24 Pages.
Communication of Opposition Proceedings for EP Application No. 17727376.0, Mail Date: Aug. 7, 2023, 10 Pages.

(56) References Cited

OTHER PUBLICATIONS

Communication pursuant to Article 71(3) EPC for EP Application No. 17727376.0, Mail Date: Jan. 13, 2021, 52 Pages.
Communication pursuant to Article 71(3) EPC for EP Application No. 19726746.1, Mail Date: Sep. 15, 2023, 37 Pages.
Communication pursuant to Article 94(3) EPC for EP Application No. 17727376.0, Mail Date: May 13, 2020, 9 Pages.
Communication pursuant to Rules 161(1) and 162 for EP Application No. 19836541.3, Mail Date: Apr. 7, 2022, 6 Pages.
Decision Rejecting Opposition issued for EP Patent Application No. 17727376.0 filed on Apr. 13, 2017, on behalf of S&R Farmaceutici S.p.A., Mail Date: Oct. 24, 2023, 36 Pages.
Decision to Grant a Patent with Eng translation for JP Application No. 2020-558023 filed on Oct. 14, 2020 on behalf of S& Farmaceutici S.P.A. Mail Date: Jul. 4, 2023, 4 pages.
Decision to Grant issued for EP Patent Application No. 19726746.1 filed on Apr. 16, 2019, on behalf of S&R Farmaceutici S.p.A., Mail Date: Sep. 15, 2023, 23 Pages.
Eng Translation of IT0001391323 for EP Application No. 17727376.0, Mail Date: May 10, 2023, 62 Pages.
Eng Translation of Priority Doc for EP Application No. 17727376.0, Mail Date: May 26, 2023, 23 Pages.
Epperly, M. V. et al., Antioxidant-Chemoprevention Diet Ameliorates Late Effects of Total-Body Irradiation and Supplements Radioprotection by MnSOD-Plasmid Liposome Administration, Radiation Research, Jun. 2011, vol. 175, pp. 759-765 (see pp. 759-761, 763-764, table 1.
First Office Action for CN Application No. 201980083492.6 filed on behalf of S& Farmaceutici S.P.A. Mail Date: Nov. 29, 2023, 5 pages.
First Office Action with English translation for CN Application No. 201980026497.5 filed on behalf of S& Farmaceutici S.P.A. Mail Date: Feb. 25, 2023, 8 pages.
First Office Action with English translation for VN Application No. 1-2020-06591 filed on Apr. 16, 2019 on behalf of S& Farmaceutici S.P.A. Mail Date: Jul. 7, 2023, 4 pages.
First Office Action with English translation for VN Application No. 1-2021-04371 filed on Jul. 16, 2021 on behalf of S& Farmaceutici S.P.A. Mail Date: Nov. 30, 2023, 4 pages.
Gerli, et al. "Biological and clinical effects of a resveratrol-based multivitamin supplement on intracytoplasmic sperm injection cycles: a single-center, randomized controlled trial," Journal of Maternal-Fetal & Neonatal Medicine, Jul. 2021, 12 pages.
Grive et al., Resveratrol improves granulosa cell activity through mitochondrial biogenesis, Fertility and Sterility, vol. 115, No. 4, Apr. 2021, 3 pages.
HUNTER P. M. et al., "Functional foods and dietary supplements for the management of dyslipidemia" Nature Reviews Endocrinology, May 2017, vol. 13, pp. 278-288.
Illiano E. et al. "Resveratrol-Based Multivitamin Supplement Increases Sperm Concentration and Motility in Idiopathic Male Infertility: A Pilot Clinical Study." J Clin Med. 2020, 10 pages.
Kim JM et al., "Role of potassium channels in female reproductive system." Obstet Gynecol Sci 2020; 63:565-76.12 pages.

Liu et al. "Resveratrol improves in vitro maturation of oocytes in aged mice and humans." Fertil Steril. May 2018;109(5):900-907. doi: 10.1016/j.fertnstert.2018.01.020. 8 pages.
Liu et al. "Resveratrol improves in vitro maturation of oocytes in aged mice and humans—Supplementary Tables" Fertil Steril. May 2018;109(5):900-907. doi: 10.1016/j.fertnstert.2018.01.020. 8 pages.
Notice of Acceptance with English translation for VN Application No. 1-2020-06591 filed on Apr. 16, 2019 on behalf of S& Farmaceutici S.P.A. Mail Date: Dec. 24, 2020, 2 pages.
Notice of Acceptance with English translation for VN Application No. 1-2021-04371 filed on Jul. 16, 2021 on behalf of S& Farmaceutici S.P.A. Mail Date: Aug. 26, 2021, 2 pages.
Notice of Opposition to EP Application No. 17727376.0, Mail Date: Mar. 22, 2022, 280 Pages.
Notice of Reasons for Refusal with Eng translation for JP Application No. 2020-558023 filed on Oct. 14, 2020 on behalf of S& Farmaceutici S.P.A. Mail Date: Jan. 13, 2023 7 pages.
Preliminary Opinion regarding opposition for EP Application No. 17727376.0, Mail Date: Apr. 3, 2023, 23 Pages.
Ragonese, et al. "Resveratrol depolarizes the membrane potential in human granulosa cells and promotes mitochondrial biogenesis," Reproductive Science, 2020. 11 pages.
Response to Communication of a Notice of Opposition to EP Application No. 17727376.0, Mail Date: Aug. 22, 2022, 54 Pages.
Response to Communication pursuant to Article 94(3) EPC for EP Application No. 17727376.0, Mail Date: Sep. 10, 2020, 8 Pages.
Second Office Action for CN Application No. 201980026497.5 filed on behalf of S& Farmaceutici S.P.A. Mail Date: Sep. 5, 2023, 5 pages.
Transmittal Decision for EP Application No. 17727376.0, Mail Date: Apr. 3, 2023, 72 Pages.
Transmittal Decision for EP Application No. 17727376.0, Mail Date: Oct. 24, 2023, 105 Pages.
Van Blerkom J. "Mitochondria as regulatory forces in oocytes, preimplantation embryos and stemcells." Reprod Biomed Online. Apr. 2008; 16(4):553-69. Review. 17 pages.
Vignali M. "Successful Mestrual Regularity and Spontaneous Pregnancies with a Resveratrol Based Multivitamin Supplement in Women with Idiopathic Premature Ovarian Insufficiency" The EuroBiotech Journal. 2022;6(1):40. 4 pages.
Written Opinion for IT Application No. ITUA20162575, Mail Date: Feb. 7, 2019, 10 Pages.
Written Submission of Oral Proceedings for EP Application No. 17727376.0, Mail Date: Aug. 2, 2023, 34 Pages.
First Office Action with Eng translation for CN Application No. 201980083492.6 filed on behalf of S&R Farmaceutici S.P.A. Mail Date: Nov. 29, 2023, 11 pages.
Mason DE et al., "Molecular basis of voltage-dependent potassium currents in porcine granulosa cells" Mol Pharmacol 2002;61:201-13.
Notice of Decision on Rejection with Eng translation for CN Application No. 201980026497.5. Mail Date: May 18, 2024, 11 pages.
Restriction Requirement for U.S. Appl. No. 17/311,669, filed Jun. 7, 2021 on behalf of S&R Farmaceutici S.P.A. Mail Date: May 16, 2024, 9 pages.
Second Office Action with Eng translation for CN Application No. 201980026497.5 filed on behalf of S&R Farmaceutici S.P.A. Mail Date: Sep. 5, 2023, 11 pages.

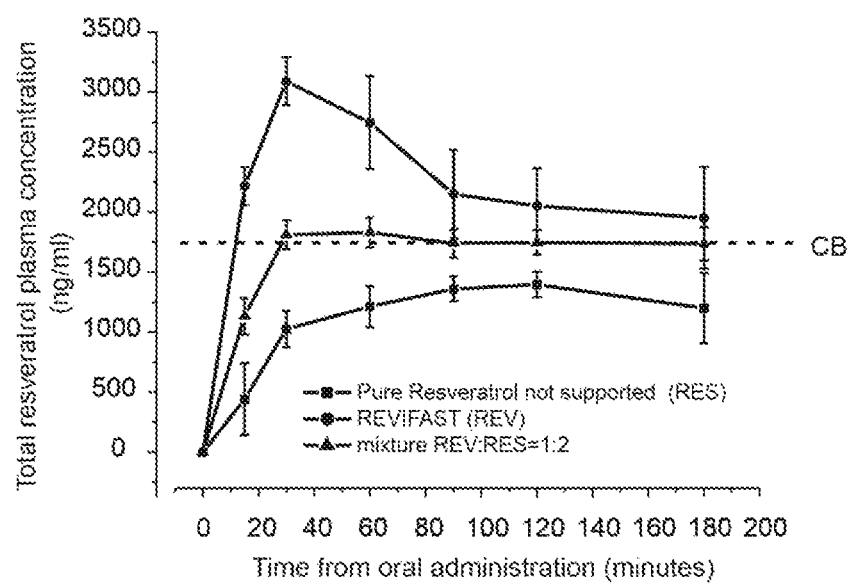

MIXTURE OF RESVERATROL SUPPORTED ON METAL HYDROXIDE AND NON-SUPPORTED PURE RESVERATROL FOR TREATING FEMALE FERTILITY

CROSS REFERENCE TO RELATED APPLICATIONS

The present application is the US national stage of International Patent Application PCT/IB2019/053137 filed on Apr. 16, 2019 which, in turn, claims priority to Italian application 102018000004540 filed on Apr. 16, 2018.

FIELD OF APPLICATION

This invention concerns the pharmaceutical, nutraceutical or in the form of a dietary supplement based on mixture of resveratrol with different kinetics of dissolution for use in the treatment of female infertility. A couple who tried to conceive for over a year without success is considered infertile or less fertile than a typical couple (Evers, 2002). The factors influencing the state of infertility are often related to women and include ovulatory insufficiency, tubal damage, endometriosis, poor egg quality and unexplained sub fertility. (Evers J L. Female subfertility. Lancet. 2002 Jul. 13; 360(9327):151-9).

To overcome these fertility problems, many couples undergo assisted Reproductive Techniques (ART). These include stimulation of ovulation, intrauterine insemination (IntraUterine inseminations, IUI), in vitro fertilization (In Vitro Fertilization, IVF) and intracytoplasmic sperm injection (ICSI). Some women use supplements with antioxidants in preparation or at the same time as treatment ART, and some women use supplements with antioxidants without practicing ART in an attempt to improve their fertility outcome.

Nutrients are defined as those organic or inorganic substances that are absorbed and assimilated by the organism through the process of digestion of food or taken through dietary supplements. Nutrients maintain homeostasis of the body composition and the state of health of an individual. Some nutrients are readily available for absorption from the food (e.g. vitamins, trace elements, antioxidants and active ingredients), others are produced during the digestive process (e.g. monosaccharides from polissaccharides or amino acids by proteins).

Many nutrients have demonstrated the ability to increase the probability of a conception, both in a natural way and through ART. Among these substances included are vitamins, provitamins, minerals and phytocomplexes, many of which have antioxidant properties. Antioxidants, in particular, are biological and chemical compounds that reduce oxidative damage (imbalance between the creation of reactive oxygen species and the ability of the body to eliminate them). Among the nutrients with anti-oxidant and non-antioxidant properties, used in female subfertility, they cite, but are not limited to: N-acetil-cysteine; Melatonin Vitamins A, C, D, E, B2, B3, B6, B12, folic acid, inositol, zinc, selenium, Coenzyme Q10, arginine, a-lipoic acid and resveratology. Showell M G, Mackenzie-Proctor R, Jordan V, Hart R J. Antioxidants for female subfertility. Cochrane Database Syst Rev. 2017 Jul. 28; 7:CD007807. In the Italian application 102016000098988, extracts of *Lycium barbarum* berries were claimed to improve female fertility.

Vitamin D is well known for its role in the maintenance of calcium homeostasis and in the promotion of bone mineralization. Increasing evidence indicates a correlation between vitamin D deficiency and decreased female fertility. Lerchbaum E, Obermayer-Pietsch B. Vitamin D and Fertility: a systematic review. Eur J Endocrinol. 2012 May; 166(5):765-78.

Vitamin E is a well-known endogenous antioxidant and the benefits of fertility include the improvement of the growth epithelium in the blood vessels and in the endometrium. Lédée-Bataille N, Olivennes F, Lefaix J L, Chaouat G, Frydman R, Delanian S. Combined treatment by pentoxifylline and tocopherol for recipient women with a thin endometrium enrolled in an oocyte donation programme. Hum Reprod. 2002 May; 17(5):1249-53.

Vitamin B6 (pyridoxine) is involved in various biochemical reactions affecting both the amino acid metabolism and that of various other compounds. Higher levels of vitamin B6 were found in fertile women than infertile women. Grajecki D, Zyriax B C, Buhling K J. The effect of micronutrient supplements on female fertility: a systematic review. Arch Gynecol Obstet. 2012 May; 285(5):1463-71. doi: 10.1007/s00404-012-2237-2.

Vitamin B12 (Cyanocoballamine) is necessary for the metabolism of fatty acids and therefore necessary for energy metabolism and cellular proliferation. Supplementation with folic acid and vitamin B-12 have been associated with positive reproductive outcomes in both natural pregnancies and those after treatment with assisted reproductive technology (ART). Gaskins A J, Chiu Y H, Williams P L, Ford J B, Toth T L, Hauser R, Chavarro J E; EARTH Study Team. Association between serum flurries and vitamin B-12 and outcomes of assisted reproductive technologies. Am J Clin Nutr. 2015 October; 102(4):943-50. Moreover, folic acid is necessary for all DNA synthesis, repair and methylation reactions, for homocysteine metabolism and in biochemical reactions involved in cell division. Dattilo M, Giuseppe D, Ettore C, Ménézo Y. Improvement of gamete quality by stimulating and feeding the endogenous antioxidant system: mechanisms, clinical results, insights on gene-environment interactions and the role of diet. J Assist Reprod Genet. 2016 December; 33(12):1633-1648.

Inositols such as my-inositol and D-chiro-inositol help ovarian function and decrease hyperandrogenism and insulin resistance. Nestler J E, D J Jakubowicz, de Vargas A F, Brik C, Quintero N, Medina F. Insulin stimulates testosterone biosynthesis by human thecal cells from women with polycystic ovary syndrome by activating its own receptor and using inositolglycan mediators as the signal transduction system. J Clin Endocrinol Metab. 1998 June; 83(6):2001-5.

Coenzyme Q10 is an important cofactor in mitochondrial physiology and its supplementation has been proposed to protect the ovarian reserve by combating mitochondrial ovarian ageing. Özcan P, Fıçıcıoğlu C, Kizilkale O, Yesiladali M, Tok O E, Ozkan F, Esrefoglu M. Can Coenzyme Q10 supplementation protect the ovarian reserve against oxidative damage? J Assist Reprod Genet. 2016 September; 33(9):1223-30.

N-Acetil cysteine is an important endogenous antioxidant molecule that has been shown to be necessary for the secretion of cervical mucus and ovulation. Badawy A, State O, Abdelgawad S. N-Acetyl cysteine and clomiphene citrate for induction of ovulation in polycystic ovary syndrome: a cross-over trial. Acta Obstet Gynecol Scand. 2007; 86(2): 218-22.

Resveratol is a polyphenol with a stilbenic structure contained in micromolar concentration in red wine and grape husk as well as in some plant species such as *Polygonum cuspidatum*. After absorption, resveratrol is subjected to reactions in metabolism: in particular, it is conjugated with sulphuric acid and glucoric acid, which therefore represent the metabolites. These metabolites can release resveratrol by acting as precursors (see for example during Enterohepatic recirculation). For this reason, when we refer to the plasmatic resveratrol we mean total resveratrol, which is the sum of free resveratrol and its metabolites. Resveratrol has been shown to protect cells from oxidative stress by behaving as an antioxidant and by improving mitochondrial function. Resveratrol is an activator of SIRT-1, a deacetylase NAD+ employee that is involved in the post-translational modification of certain proteins.

SIRT-1's are involved in epigenetic regulation, as there are histone proteins among their target proteins. Through the activation of SIRT-1 resveratrol has been suggested to prevent ovarian ageing, as demonstrated by the decrease in the frequency of mitotic errors and by the mitochondrial distribution, thus allowing the maintenance of Ovarian reserve (Li et al., 2013). During the in vitro maturation of resveratrol supplementation improves oocyte quality and embryonic development (Tatone et al., 2018). Liu M, Yin Y, Ye X, Zeng M, Zhao Q, Keefe D L, Liu L. Resveratrol protects against age-associated infertility in mice. Hum Reprod. 2013 March; 28(3):707-17. Tatone C, Di Emidio G, Barbonetti A, Carta G, Luciano A M, Falone S, Amicarelli F. Sirtuins in gamete biology and reproductive physiology: emerging roles and therapeutic potential in female and male infertility. Hum Reprod Update. 2018.

Resveratrol possesses an optimal breakdown coefficient to cross the biological membranes, but the absorption and therefore its bioavailability is limited by the low solubility in water. Molecules such as resveratrol (membrane permeable, but poorly soluble in water) are classified according to the biopharmaceutical system in class II and their absorption can be increased by increasing the dissolution rate. Resveratrol formulations co-precipitated or supported with bivalent or trivalent metal salts, known in the art as described in the patent application EP 2679243 whose contents are here completely incorporated by reference, present a better dissolving speed versus a pure resveratrol not supported.

According to a particularly preferred form of accomplishment, a formulation containing trans-Resveratrol supported on magnesium hydroxide is used in the composition according to the invention. The content of Trans-resveratrol in such formulation can be between 10% and 50% by weight on the weight of the formulation, preferably it is 30% by weight on the weight of the formulation and sold commercially under the trade name REVIFAST®. REVIFAST® presents an increased dissolution rate at the pH of the gastric environment compared to unsupported pure resveratrol. Non-supported pure resveratrol means a crystalline product with a purity exceeding 98% of both natural origin (e.g. *Polygonum cuspidatum*) and synthesis or mixtures of the two.

In the patent application US2017/0312251 is reported a formulation of dietary supplements to increase female fertility. The Formulation has a composition that includes L-carnitine tartrate, coenzyme Q10, vitamin B12, N-acetyl cysteine and plant extracts containing various antioxidants including resveratrol. In Addition, a dosage plan is claimed which includes a fractional daily dosage (2 cps/day) of the formulation described above for a period of at least three months.

In the PCT/IB2017/052151 patent application, a formulation is claimed including a mixture of inositols in precise stoichiometric ratios and resveratrol co-precipitated or supported with bivalent or trivalent Salts in the form of hydroxides able, among the various applications, to reduce the symptomatology associated with polycystic ovary syndrome, including infertility.

After ingestion and absorption of a single dose of the nutrient, the plasma concentration increases until it reaches a peak of maximum concentration, after which it decreases until it disappears over time following processes related to metabolism, distribution and elimination of nutrients.

The physiological action of the nutrient is partly mediated by the chemical-physical interaction of the same with specific receptors present in our organism. Receptor means a protein, a nucleic acid or a lipid that has the ability, on the one hand, to interact with the nutrients and on the other to modify the biochemical reactions within the cells expressing the above-mentioned receptors. The nutrient interaction with the receptor leads to the formation of a nutrient/receptor complex hereinafter referred to as the complex. The formation of the complex is through the formation of chemical bonds between the nutrient and the receptor and can be described by the chemical reaction shown in diagram 1:

Nutrient+Receptor<->Complex [scheme 1]

The affinity of a nutrient for its receptor means the energy associated with the formation of the complex and expresses the tendency of a nutrient to associate with a receptor or to remain free. At the same affinity of a nutrient for its receptor the concentration of the complex is solely dependent on the nutrient concentration according to the scheme 1.

The efficacy of a complex means the ability of the complex to activate, inhibit or modify biochemical reactions within the cell and between cells. The efficacy of a complex determines the biological effect of the nutrient itself on the organism according to the pattern 2.

Nutrient+Receptor<->Complex->biological effect [scheme 2]

From the above, a nutrient evokes a biological effect in precise concentration ranges that are closely related to the affinity for the receptor (s) that mean/no the biological effect. The therapeutic range of a substance is the range of concentrations that can actually evoke a therapeutically effective biological effect. This range is subjective and can vary significantly from patient to patient, and obviously from substance to substance. When a substance such as a drug or nutrient is administered in a preventive manner, as in the case of the object of this invention, it is reasonable to use the target level strategy. In particular, a concentration of the desired stationary state (target concentration, CB) of the drug or nutrient (usually in the plasma) is chosen and a dosage is calculated to allow it to reach this value. Except when you do not have specific information about the drug and nutrient, the target concentration represents the center of the Therapeutic range. It Is generally accepted that side effects or loss of efficacy of a nutrient are related to the difficulty of quickly reaching and maintaining the target concentration of the drug or nutrient in a specific therapeutic window. (Goodman & Gilman, The pharmacological bases of the therapy, Zanichelli 8 edition, 1992). Many biological effects of nutrients are observed in vitro, a condition where the concentration of the same can be defined by the experimenter and is stable over time. Unfortunately, the concentration reached by a nutrient in vivo is not constant but dynamic and takes some time, from the time of administration, to reach and maintain the target concentration. Due to this dynamic concentration many biological effects observed in vitro cannot be reproduced in vivo. The rapid attainment of the target concentration of the nutrient and its maintenance would theoretically allow to overcome the limits posed by the complexity of the biological systems in vivo.

Surprisingly, the applicant found that the administration of a composition of resveratrol supported on hydroxides of bivalent or trivalent metals, particularly on magnesium hydroxide together with pure non-supported resveratrol, allows the concentration of the molecule to reach and maintain a target concentration useful for improving female fertility.

BRIEF DESCRIPTION OF THE FIGURES

FIG. 1. Plasma profile of total resveratrol (free resveratrol+its metabolites) following the administration to voluntary subjects of a single dose of resveratrol of 180 mg REVIFAST® (circles), from pure resveratrol not supported (squares) and a simulation of the combination of resveratrol from REVIFAST® and pure resveratrol not supported in the ratio 1:2 (triangles). A dotted line shows the value of the target concentration (CB).

SUMMARY OF THE INVENTION

The Applicant is designed with a composition or formulation comprising resveratrol supported on bivalent or trivalent metal hydroxide and unsupported pure resveratrol, which are present in specific stoichiometric ratios and have different speeds of dissolution when administered, is able to:
a) Rapidly reach the target concentration of total resveratrol;
b) Increase the duration that the plasma concentration of total resveratrol maintains at the target concentration (CB);
c) To increase fertility outcome In fact, as demonstrated in the experimental part given below, the applicant found, surprisingly, by means of food supplements of resveratrol having different dissolution rates in reports defined stoichiometry increases the rate of pregnancy in women.

In the composition according to the invention, the term "formulation" means a mixture comprising: Resveratrol with different dissolution rates as defined above and nutrients with antioxidant properties used in female subfertility as N-Acetil-cysteine; Melatonin Vitamins A, C, D, E, B2, B3, B6, B12, folic acid, inositol, zinc, selenium, Coenzyme Q10, A-lipoic acid, arginine and extracts from the berries of the *Lycium barbarum*.

Preferably, in the composition according to the invention, the total amount of resveratrol administered daily is between 20 mg and 300 mg, preferably between 150 and 180 mg even more precisely 150 mg.

Preferably, in the composition according to the invention, the relationship between resveratrol supported on hydroxides of bivalent or trivalent metals (in particular resveratrol arising from REVIFAST®) and that resulting from a pure resveratrol unsupported is Between 0.1 and 10, preferably between 0.3 and 3 even more preferably 0.5.

Preferably, in the composition according to the invention, the unsupported pure resveratrol is a crystalline product also in the form of granulated with a purity greater than 98% both of natural origin (for example from *Polygonum cuspidatum*) that of synthesis or Mixtures of the two.

Preferably, in the composition according to the invention, the quantity of N-acetil-cysteine administered daily is between 100 mg and 1000 mg, preferably between 200 and 800 mg even more preferably 600 mg.

Preferably, in the composition according To the invention, the quantity of vitamins A daily administered is between 200 IU and 2000 micrograms, preferably between 500 and 1500 micrograms even more preferably 1200 micrograms.

Preferably, in the composition according to the invention, the quantity of vitamins C administered daily is between 100 mg and 1500 mg, preferably between 300 and 1200 mg even more preferably 1000 mg.

Preferably, in the composition according to the invention, the quantity of vitamins administered daily is between 10 200 mg, preferably between 20 and 100 mg IU even more preferably 60 mg.

Preferably, in the composition according to the invention, the quantity of vitamins B2, administered daily is between 0.5 mg and 50 mg, preferably between 1 and 30 mg even more preferably 15 mg.

Preferably, in the composition according to the invention, the quantity of vitamins B3, administered daily is between 10 mg and 100 mg, preferably between 20 and 70 mg even more preferably 50 mg.

Preferably, in the composition according to the invention, the quantity of betaine, administered daily is between 20 mg and 1000 mg, preferably between 100 and 500 mg even more preferably 200 mg.

Preferably, in the composition according to the invention, the amount of vitamins B6, administered daily is between 0.5 mg and 10 mg, preferably between 1 and 8 mg even more preferably 3 mg.

Preferably, in the composition according to the invention, the quantity of vitamin B12, administered daily is between 0.5 micrograms and 2000 micrograms, preferably between 2 micrograms and 500 micrograms even more preferably 10 micrograms.

Preferably, in the composition according to the invention, the amount of folic acid or reduced and methylated forms such as the 5-Methyl-Tedra-Hydro-folate administered daily is between 50 mcg and 800 mcg, preferably between 200 mcg and 500 mcg even more Preferably 400 mcg.

Preferably, in the composition according to the invention, the quantity of Inositols with particular attention to my-inositol and the Chiro-inositol, which administered daily are between 10 mg and 1000 mg, preferably between 100 and 800 mg even more Preferably 700 mg.

Preferably, in the composition according to the invention, the quantity of zinc administered daily is between 1 mg and 100 mg, preferably between 5 and 50 mg even more preferably 15 mg.

Preferably, in the composition according to the invention, the amount of selenium, administered daily is between 30 mcg and 200 mcg, preferably between 50 and 100 mcg even more preferably 70 mcg.

Preferably, in the composition according to the invention, the quantity Coenzyme Q10, administered daily is between 100 mg and 500 mg, preferably between 150 and 400 mg even more preferably 200 mg.

Preferably, in the composition according to the invention, the amount of a-lipoic acid, administered daily is between 10 mg and 300 mg, preferably between 20 and 200 mg even more preferably 150 mg.

Preferably, in the composition according to the invention, the amount of arginine, administered daily is between 100 mg and 1000 mg, preferably between 200 and 500 mg even more preferably 280 mg.

Example 1

The pharmacokinetics in humans of different types of resveratrol formulations. The administration of 180 mg Resveratrol supported on magnesium hydroxide (REVIFAST®) in voluntary subjects leads to a transient increase in total concentration (free resveratrol+resveratrol metabolites) plasmatic resveratrol with Time at the peak concentration of 30 minutes from administration, followed by a decay of about 40% in the period up to 180 minutes from administration. On the contrary, the total plasma concentration of resveratrol achieved with 180 mg of pure resveratrol results in absolute lesser value and with a time at a peak of 90 minutes from administration. The simulation of the combination of resveratrol with different dissolving kinetics REVIFAST®+ pure resveratrol not supported in report 1:2) shows a spike in plasma concentration of total resveratrol (Target Concentration, CB) with a peak time of 30 minutes that is kept stable throughout the period examined (180 minutes).

Example 2.

An illustrative table with the formulation of the composition according to the invention is described below

| Component | Dose |
| --- | --- |
| REVIFAST® 30% resveratrol | 160 mg (of which 48 mg di resveratrol) |
| Sintetic resveratrol 98% resveratrol | 104 mg (of which 102 mg di resveratrol) |
| Total resveratrol | 150 mg |

The composition described in Example 1 can be contained in a variety of formulations such as: capsules, tablets, syrups, suspensions and emulsions. The formulation of Example 2 can be supplemented with nutrients with antioxidant properties and not used in female subfertility such as N-acetil-cysteine; Melatonin Vitamins A, C, D, E, B2, B3, B6, B12, folic acid, inositol, zinc, selenium, Coenzyme Q10, A-lipoic acid, betaine and berry extracts of *Lycium barbarum*.

Example 3.

Another illustrative table with the formulation of the composition according to the invention is described below:

| Componente | Dose |
| --- | --- |
| REVIFAST® 30% resveratrolo ponderale | 160 mg (di cui 48 mg di resveratrolo) |
| Resveratrolo sintetico 98% resveratrolo ponderale | 104 mg (di cui 102 mg di resveratrolo) |
| Acido folico (5-Metil-Tedra-Idro-folato) | 400 microgrammi |
| Vitamina D3 | 25 microgrammi |
| Vitamina B6 | 1.4 mg |
| Vitamina B12 | 2.5 microgrammi |

The formulations of examples 2 and 3 also include possible excipients, technological additives, co-formularies, polar and semipolar polymeric matrices, carriers and stabilizers for both pharmaceutical and nutraceutical use. Examples of excipients are xanthan gum and guar gum, sweeteners such as glucose and sucrose, acidic substances such as citric acid agents such as stearic acid. The composition described in Example 2 can be contained in a variety of formulations such as: capsules, tablets, syrups, suspensions and emulsions. The formulations referred to in examples 2 and 3 may be administered by splitting them several times a day, preferably twice daily.

Example 4.

Case report n1 of fertility enhancement

Ms. MM is 37 years old and is classified as infertile since has tried to conceive for more than 12 months without the initiation of a state of pregnancy. She is not affected by polycystic ovary syndrome according to the Rotterdam criteria. She was supported with a food supplement according to the scheme for 3 months based on pure resveratrol (100 mg per day) without having a pregnancy and subsequently doubling the dosage (200 mg) has not changed its situation. Ms. MM then added a REVIFAST®-based supplement (48 mg/day) together with a non-supported pure Resveratrol-based supplement (100 mg/day) for a period of three months after which she successfully began a pregnancy As, demonstrated by the sonographic framework. The quantities taken by Ms MM are such that the dosage used is that shown in examples 2 and 3.

Example 5.

Case report n2 of fertility enhancement

Miss. CL, a 32 year old women classified as being sub-fertile because she has been trying to conceive for more than 12 months unsuccessfully. She is not affected by metabolic disorders such as polycystic ovary syndrome according to the Rotterdam criteria. In her dietary supplement scheme, she took a resveratrol supplement supported on magnesium hydroxide (48 mg daily) for 2 months without having a pregnancy. Subsequently, on her own initiative, Ms CL changed her integration scheme by adding a supplement of unsupported pure resveratrol (100 mg per day). After a period of 53 days she resulted pregnant as shown by the ultrasound picture. The quantities assumed by Ms CL are such that the dosage used is that shown in examples 2 and 3.

Example 6. Case Report n3 of Fertility Enhancement

Ms. TB is 39 years old and is classified as a sub-fertile because she has been trying to conceive for more than 12 months without starting a state of pregnancy. It is not affected by metabolic disorders such as polycystic ovary syndrome according to the Rotterdam criteria. In his dietary supplement scheme he took a resveratrol supplement supported on magnesium hydroxide (48 mg per day)+inositol (1400 mg) for 2 months daily without becoming pregnant. Subsequently, on her own initiative, Ms TB changed her integration scheme by adding a supplement of unsupported pure resveratrol (100 mg per day). After a period of 68 days she had a pregnancy as shown by the ultrasound picture. The quantities assumed by Ms TB are such that the dosage used is that shown in examples 2 and 3

The invention claimed is:
1. A pharmaceutical or nutraceutical composition or food supplement comprising a mixture of resveratrol supported on at least one divalent and/or trivalent metal hydroxide and of non-supported pure resveratrol synthetized or natural, in an effective amount for treatment of female Infertility in human species.

2. The pharmaceutical or nutraceutical composition or food supplement according to claim 1, in which the at least one divalent and/or trivalent metal hydroxide comprises magnesium hydroxide.

3. The pharmaceutical or nutraceutical composition or food supplement according to claim 1, wherein the stoichiometric ratio between the resveratrol supported on at least one divalent and/or trivalent metal hydroxide and the non-supported pure resveratrol is included between 0.1 and 10.

4. The pharmaceutical or nutraceutical composition or food supplement according to claim 1, further comprising nutrients with antioxidant properties and not used in female subfertility selected from N-acetyl-cysteine. Melatonin. Vitamins A, C, D, E, B2, B3, B6, B12, folic acid, inositol, zinc, selenium, Coenzyme Q10, A-lipoic acid, arginine and *Lycium barbarum* berry extracts.

5. The pharmaceutical or nutraceutical composition or food supplement according to claim 1, wherein the composition or food supplement is prepared in a pharmaceutical, nutraceutical or food-based form chosen from: capsules, tablets, syrups, suspensions and emulsions.

6. The pharmaceutical or nutraceutical composition or food supplement of claim 1, wherein the stoichiometric ratio between the resveratrol supported on at least one divalent and/or trivalent metal hydroxide and the pure one is between 0.3 and 3.

7. The pharmaceutical or nutraceutical composition or food supplement of claim 1, wherein the stoichiometric ratio between the resveratrol supported on.

8. The pharmaceutical or nutraceutical composition or food supplement according to claim 4, wherein the nutrient are selected from N-acetyl-cysteine, Melatonin, Vitamins A, C, D, E, B2, B3, B6, B12, folic acid, inositol, zinc, selenium, Coenzyme Q10, A-lipoic acid, arginine and *Lycium barbarum* berry extracts.

9. A method of maintaining ovarian reserve in a subject, comprising
administering an effective amount of the pharmaceutical or nutraceutical composition or food supplement of claim 1 to the subject.

10. A method of improving ovary quality in a subject, comprising
administering an effective amount of the pharmaceutical or nutraceutical composition or food supplement of claim 1 to the subject.

11. A method of treating female infertility in human, comprising:
administering an effective amount of the pharmaceutical or nutraceutical composition or food supplement of claim 1 to a subject suffering from female infertility.

12. The method of claim 11, wherein the composition or food supplement is prepared in a pharmaceutical, nutraceutical or food-based form selected from: capsules, tablets, syrups, suspensions and emulsions.

13. The method of claim 11, wherein the supported resveratrol is resveratrol supported on magnesium hydroxide.

14. The method of claim 11, wherein the stoichiometric ratio between the resveratrol supported on at least one divalent and/or trivalent metal hydroxide and the pure one is included between 0.1 and 10.

15. The method of claim 11, wherein the stoichiometric ratio between the resveratrol supported on at least one divalent and/or trivalent metal hydroxide and the pure one is included between 0.3 and 5.

16. The method of claim 11, wherein the composition or food supplement further comprises nutrients with antioxidant properties and not used in female subfertility such as N-acetyl-cysteine, Melatonin, Vitamins A, C, D, E, B2, B3, B6, B12, folic acid, inositol, zinc, selenium, Coenzyme Q10, A-lipoic acid, arginine and *Lycium barbarum* berry extracts.

17. The method of claim 11, wherein the composition or food supplement is administered two times daily for a treatment period of 3 months.

18. The method of claim 11, wherein the composition or food supplement comprises a fractional dally dosage of the mixture.

* * * * *